(12) United States Patent
Kano et al.

(10) Patent No.: US 7,268,236 B2
(45) Date of Patent: Sep. 11, 2007

(54) METHOD OF HEIGHTENING OPTICAL PURITY OF 1-BENZYL-3-AMINOPYRROLIDINE AND SALT FOR USED THEREIN

(75) Inventors: Fumihiko Kano, Kobe (JP); Natsuki Mori, Kakogawa (JP)

(73) Assignee: Kaneka Corporation, Osaka (JP)

(*) Notice: Subject to any disclaimer, the term of this patent is extended or adjusted under 35 U.S.C. 154(b) by 479 days.

(21) Appl. No.: 10/490,267

(22) PCT Filed: Mar. 28, 2003

(86) PCT No.: PCT/JP03/03933

§ 371 (c)(1),
(2), (4) Date: Mar. 22, 2004

(87) PCT Pub. No.: WO03/082815

PCT Pub. Date: Oct. 9, 2003

(65) Prior Publication Data

US 2004/0249169 A1 Dec. 9, 2004

(30) Foreign Application Priority Data

Mar. 29, 2002 (JP) ............................. 2002-096404

(51) Int. Cl.
*C07D 207/14* (2006.01)
(52) U.S. Cl. ..................................... 548/557
(58) Field of Classification Search ............. 548/557
See application file for complete search history.

(56) References Cited

U.S. PATENT DOCUMENTS 4,910,319 A * 3/1990 Krebs et al. ............. 548/557
5,653,997 A * 8/1997 Renimel et al. ........... 424/450
5,696,273 A * 12/1997 Andre et al. ............. 548/531
5,977,381 A    11/1999 Klinkhammer et al.
6,423,689 B1 * 7/2002 Booth et al. ............. 514/19

FOREIGN PATENT DOCUMENTS

| JP | 2-218664 A | 8/1990 |
|----|---|---|
| JP | 6-340599 A | 12/1994 |
| JP | 7-506110 A | 7/1995 |
| JP | 9-124595 A | 5/1997 |
| JP | 9-176115 A | 7/1997 |
| JP | 9-216866 A | 8/1997 |
| JP | 2000-53642 A | 2/2000 |
| WO | WO93-22283 A1 | 11/1993 |

OTHER PUBLICATIONS

Shiraiwa, et al. "Synthesis of optically active 1,4-thiazane-3-carboxylic acid via optical resolution by preferential crystallization of (RS)-2-amino-3-{(2-chlorethyl) sulfanyl} propanoic acid hydrochloride", Bioscience, Biotechnology and Biochemistry, (1998), 62 (12) 2382-2387.
Jean, Ludovic et al, "A Convenient Route to 1-benzyl 3-aminopyrrolidine and 3-aminopiperidine", *Tetrahedron Letters* 42 (2001) pp. 5645-5649.

* cited by examiner

*Primary Examiner*—Golam M. M. Shameem
(74) *Attorney, Agent, or Firm*—Sughrue Mion PLLc.

(57) ABSTRACT

The present invention provides a method to improve the optical purity of 1-benzyl-3-aminopyrrolidine having a low optical purity using an inexpensive agent via a simple procedure. The present invention provides a method for improving the optical purity of 1-benzyl-3-aminopyrrolidine including the steps of converting 1-benzyl-3-aminopyrrolidine into an equimolar salt with an optically inactive acid, and recovering the salt as crystals. The present invention also provides a salt of 1-benzyl-3-aminopyrrolidine that is used in the method.

17 Claims, No Drawings

METHOD OF HEIGHTENING OPTICAL PURITY OF 1-BENZYL-3-AMINOPYRROLIDINE AND SALT FOR USED THEREIN

TECHNICAL FIELD

The present invention relates to a method for improving the optical purity of 1-benzyl-3-aminopyrrolidine, which is useful as a synthetic intermediate in fine chemicals such as medicines and agricultural chemicals. The present invention also relates to a new salt of 1-benzyl-3-aminopyrrolidine, which is used in the method to improve the optical purity.

BACKGROUND ART

The following methods used to improve the optical purity of 1-benzyl-3-aminopyrrolidine are well known. For example, racemic 1-benzyl-3-aminopyrrolidine is optically resolved with an optically active carboxylic acid derivative (Japanese Unexamined Patent Application Publication No. 02-218664); an optically active amino acid derivative or an optically active tartaric acid derivative is used as an optical resolution agent (Japanese Unexamined Patent Application Publication Nos. 09-124595 and 09-176115); and an optically active camphorsulfonic acid is used as the optical resolution agent (Japanese Unexamined Patent Application Publication No. 09-216866). However, none of the above optical resolution agents are readily available and are inexpensive. Therefore, these methods are unsatisfactory for industrial production.

In terms of an alternative method, an optically active material is converted to a pyrrolidine derivative in order to produce optically active 1-benzyl-3-aminopyrrolidine. However, this compound is often racemized during the derivation process; therefore, it is difficult to produce high-optical-purity 1-benzyl-3-aminopyrrolidine (for example, Japanese Unexamined Patent Application Publication No. 2000-53642, PCT Japanese Translation Patent Publication No. 07-506110, etc.). Consequently, there is a demand for the development of a method to improve the optical purity of 1-benzyl-3-aminopyrrolidine produced by these methods.

In addition to the salt of 1-benzyl-3-aminopyrrolidine with an optically active acid described above, racemic 1-benzyl-3-aminopyrrolidine monohydrochloride (Tetrahedron Letters 42 (2001) 5,645), optically active 1-benzyl-3-aminopyrrolidine dihydrochloride (Japanese Unexamined Patent Application Publication No. 02-218664), and racemic 1-benzyl-3-aminopyrrolidine monofumarate are disclosed. However, no method has been reported to improve the optical purity of 1-benzyl-3-aminopyrrolidine by forming the salts thereof.

As described above, a method to improve the optical purity of 1-benzyl-3-aminopyrrolidine having a low optical purity using an inexpensive agent via a simple procedure is unknown.

SUMMARY OF THE INVENTION

In view of the above problems, it is an object of the present invention to provide a method to improve the optical purity of 1-benzyl-3-aminopyrrolidine having a low optical purity using an inexpensive agent via a simple procedure.

As a result of intensive study to solve the above problems, the present inventors have found that high-optical-purity 1-benzyl-3-aminopyrrolidine can be inexpensively and simply produced by converting 1-benzyl-3-aminopyrrolidine into an equimolar salt with an optically inactive acid and recovering the salt as crystals, and have successively achieved the present invention.

The present invention relates to a method to improve the optical purity of 1-benzyl-3-aminopyrrolidine. The method includes the steps of converting 1-benzyl-3-aminopyrrolidine into an equimolar salt with an optically inactive acid, and then recovering the salt as crystals.

The present invention also relates to a salt of 1-benzyl-3-aminopyrrolidine represented by general formula (1):

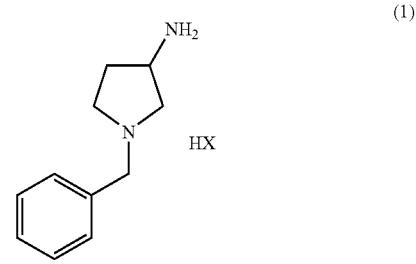

(wherein HX represents hydrobromic acid, methanesulfonic acid, or acetic acid).

DISCLOSURE OF INVENTION

The present invention will now be described in detail.

According to the method used to improve the optical purity of 1-benzyl-3-aminopyrrolidine in the present invention, 1-benzyl-3-aminopyrrolidine, in particular, its optically active substance, is converted into an equimolar salt with an optically inactive acid, and the salt is then recovered as crystals.

Low-optical-purity 1-benzyl-3-aminopyrrolidine used in the present invention can be prepared as follows. For example, as is disclosed in Japanese Unexamined Patent Application Publication No. 2000-53642, a 1,2,4-trisubstituted butane derivative is converted into a pyrrolidine derivative in the presence of a primary amine, followed by reaction of the pyrrolidine derivative under pressure in the presence of another amine. As is disclosed in PCT Japanese Translation Patent Publication No. 07-506110, amino group-protected L-aspartic acid is reduced, and then the product is allowed to react with, for example, a thionyl halide. Furthermore, the product is allowed to react with an amine to produce a pyrrolidine derivative, and then the pyrrolidine derivative is deprotected.

Examples of the optically inactive acid used in the present invention include a mineral acid such as hydrochloric acid, hydrobromic acid, phosphoric acid, and sulfuric acid; an organic sulfonic acid such as methanesulfonic acid; and a carboxylic acid such as acetic acid. These acids may be used alone or in combination. A monovalent acid such as hydrochloric acid, hydrobromic acid, methanesulfonic acid, and acetic acid is preferably used, because these acids readily form an equimolar salt with 1-benzyl-3-aminopyrrolidine. In terms of the properties of the crystals, such as low hygroscopicity and good filterability, hydrobromic acid and methanesulfonic acid are more preferably used.

The content of the optically inactive acid is not limited, as long as the optically inactive acid can form an equimolar salt with 1-benzyl-3-aminopyrrolidine, and the salt can then be recovered as crystals. In order to significantly improve the optical purity without forming a salt of 1-benzyl-3-aminopyrrolidine with the optically inactive acid in a ratio of 1:2 by mole, the content of the optically inactive acid is preferably 0.1 molar equivalents to 1 molar equivalent, and more preferably, 0.5 molar equivalents to 0.9 molar equivalents of 1-benzyl-3-aminopyrrolidine. The content of the optically inactive acid may be 1 molar equivalent or less of one optical isomer having a higher content of 1-benzyl-3-aminopyrrolidine, thereby maximizing the improvement of the optical purity.

The procedure to improve the optical purity of the present invention is preferably carried out in a solvent. Examples of the solvent used in the present invention include alcohols such as isopropyl alcohol, ethanol, and methanol; polyhydric alcohols such as ethylene glycol and propylene glycol; esters such as ethyl acetate and methyl acetate; hydrocarbons such as toluene and hexane; ethers such as diethyl ether, tetrahydrofuran, and methyl-tert-butylether; polyethers such as glymes; halogenated hydrocarbons such as methylene chloride; amides such as dimethylformamide; sulfoxides such as dimethylsulfoxide; and water. Preferably, esters such as ethyl acetate; hydrocarbons such as toluene and hexane; alcohols such as isopropyl alcohol and ethanol; and water are used. These solvents may be used alone or in combination.

The kind, content, and mixing ratio of the solvents may be selected in view of the solubility of the desired salt.

The methods used to crystallize the equimolar salt of 1-benzyl-3-aminopyrrolidine and the optically inactive acid are as follows:

(1) An aqueous solution of an optically inactive acid is mixed with 1-benzyl-3-aminopyrrolidine, and the mixture is then concentrated to remove water, thus crystallizing the salt. A solvent that can form an azeotropic mixture with water (for example, ethyl acetate and toluene) may be used. In this case, water may be removed by azeotropy.

(2) An optically inactive acid is mixed with 1-benzyl-3-aminopyrrolidine in a solvent to crystallize the salt.

(3) An optically inactive acid is mixed with 1-benzyl-3-aminopyrrolidine in a solvent, alternatively, a salt of 1-benzyl-3-aminopyrrolidine with an optically inactive acid is dissolved in a solvent; and then the resultant mixture is cooled to crystallize the salt.

(4) An optically inactive acid is mixed with 1-benzyl-3-aminopyrrolidine in a solvent; alternatively, a salt of 1-benzyl-3-aminopyrrolidine with an optically inactive acid is dissolved in a solvent. A poor solvent is then added to the resultant mixture to crystallize the salt. Alternatively, the solvent in the resultant mixture is replaced with a poor solvent to crystallize the salt.

A suitable method may be selected in view of the combinations of the kinds of salt and the solvent. For example, when using an acid such as hydrochloric acid or hydrobromic acid, both of which are readily used as an aqueous solution, method (1) is preferably selected. When using an acid such as methanesulfonic acid or acetic acid, both of which are generally and readily used in anhydrous form, method (2) is preferably selected. Furthermore, salt slurry produced by method (1) or (2) may be redissolved by method (3), and then the mixture is cooled to crystallize the salt. Thus, methods (1), (2), (3) and (4) may be satisfactorily performed in combination to crystallize the salt.

Examples of the solvents used in methods (2), (3), and (4) include the same solvents described above.

Examples of the poor solvent used in method (4), include toluene and hexane.

The salt of 1-benzyl-3-aminopyrrolidine with an optically inactive acid used in method (3) or (4) may be prepared by the method described in the present invention (i.e., method (1), method (2), method (3) wherein an optically inactive acid is mixed with 1-benzyl-3-aminopyrrolidine in a solvent, or method (4) wherein an optically inactive acid is mixed with 1-benzyl-3-aminopyrrolidine in a solvent). The salt of 1-benzyl-3-aminopyrrolidine with an optically inactive acid prepared by the above method may be used again in method (3) or (4). Alternatively, the salt of 1-benzyl-3-aminopyrrolidine with an optically inactive acid used in method (3) or (4) may be prepared during a process to synthesize 1-benzyl-3-aminopyrrolidine in the presence of an optically inactive acid. The salt of 1-benzyl-3-aminopyrrolidine with an optically inactive acid prepared by the above process may be used in method (3) or (4).

When a salt of 1-benzyl-3-aminopyrrolidine with an optically inactive acid is dissolved in a solvent, for example, the mixture may be heated. Although the temperature of the mixture during dissolution is not limited, the dissolution may be appropriately performed at a temperature that allows 1-benzyl-3-aminopyrrolidine and the optically inactive acid to be dissolved in the solvent or the mixed solvent, or higher.

The temperature of the solution during the crystallization in methods (1) to (4) may be suitably determined in view of the kinds of salt and solvent, and is not limited. The crystallization may be preferably performed at a temperature lower than the temperature that allows 1-benzyl-3-aminopyrrolidine and the optically inactive acid to be dissolved in the solvent or the mixed solvent. The temperature of the solution during the crystallization may be appropriately determined in view of the desired amount of precipitation.

The crystals of the equimolar salt of 1-benzyl-3-aminopyrrolidine and the optically inactive acid precipitated by the crystallization method described above can be separated by, for example, filtration to recover the crystals.

Since the equimolar salt of 1-benzyl-3-aminopyrrolidine and the optically inactive acid crystallized by the method has not only a high optical purity but also a high chemical purity, the salt can be used directly as a material for fine chemicals such as medicines and agricultural chemicals. Furthermore, the salt may be treated with a base such as an alkali metal hydroxide to isolate 1-benzyl-3-aminopyrrolidine. The product may then be, for example, extracted, concentrated, and distilled to produce oily 1-benzyl-3-aminopyrrolidine having a high optical purity.

Among the equimolar salts of 1-benzyl-3-aminopyrrolidine and the optically inactive acids, a salt with hydrobromic acid, methanesulfonic acid, or acetic acid, in particular, its optically active substance is a new compound in which the present inventors found its utility in the method to improve the optical purity of 1-benzyl-3-aminopyrrolidine, the salt being represented by general formula (1):

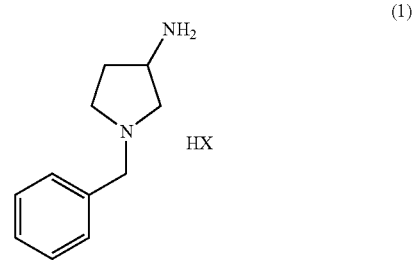

(1)

(wherein HX represents hydrobromic acid, methanesulfonic acid, or acetic acid).

BEST MODE FOR CARRYING OUT THE INVENTION

The present invention will now be described in detail with reference to the following examples, which do not serve to limit the scope of the present invention.

The optical purity in the following Examples was determined by the following method. A solution (0.2 mL) of 0.4% GITC (GITC: 2,3,4,6-tetra-O-acetyl-β-D-glucopyranosyl thiocyanate) in acetonitrile was added to a solution (0.1 mL) of 0.18% 1-benzyl-3-aminopyrrolidine in acetonitrile. (When the optical purity of a salt of 1-benzyl-3-aminopyrrolidine with an optically inactive acid was determined, oily 1-benzyl-3-aminopyrrolidine prepared by the following procedure was used for the analysis. The salt of 1-benzyl-3-aminopyrrolidine with an optically inactive acid was dissolved in water, and sodium hydroxide was then added to alkalify the solution. The solution was extracted with toluene and then concentrated to recover oily 1-benzyl-3-aminopyrrolidine.) The solution containing a mixture of GITC and 1-benzyl-3-aminopyrrolidine was allowed to react for 10 minutes at room temperature, and a solution (0.1 mL) of 0.2% ethanolamine in acetonitrile was then added to the solution and allowed to stand for 3 minutes. Subsequently, the solution was diluted with 0.05% aqueous phosphoric acid solution (1.0 mL) to prepare a sample solution. The sample solution (5 µL) was injected into a high performance liquid chromatograph (HPLC). The optical purity was determined by the ratio of peak areas measured by liquid chromatography. The column used for the analysis was a CAPCELL PAK C18 SG120 (SISEIDO), 4.6 mm in diameter by 250 mm in length. The mobile phase was a mixture (62:38 by volume) of an aqueous solution with a pH of 4 (the aqueous solution was prepared by adding a 5% aqueous acetic acid solution to a 0.03% aqueous ammonia solution) and methanol. The flow rate was 1.0 mL/min., the temperature of the column was 30° C., and the detection wavelength was 254 nm in the ultraviolet region. The detection time of the GITC derivative of (R)-1-benzyl-3-aminopyrrolidine was 25.5 minutes, and the detection time of the GITC derivative of (S)-1-benzyl-3-aminopyrrolidine was 28.5 minutes.

EXAMPLE 1

1-Benzyl-3-aminopyrrolidine (1.50 g) having a chemical purity of 89.9 weight percent and an optical purity of 88.8% e.e. ((R) enantiomeric excess) was dissolved in ethyl acetate (10 g). Concentrated hydrochloric acid (0.75 g, i.e., an amount of 1.0 molar equivalent of the (R)-1-benzyl-3-aminopyrrolidine) was added to the mixture. The solution was concentrated under reduced pressure to remove water. Ethyl acetate (20 mL) was added to the concentrated mixture, and the mixture was further concentrated. Ethyl acetate (20 mL) was added to the resultant mixture, and the mixture was left for crystallization. The crystals were filtrated and then dried to recover 1-benzyl-3-aminopyrrolidine monohydrochloride (1.48 g). The optical purity was increased to 93.6% e.e. ((R) enantiomeric excess).

EXAMPLE 2

As in Example 1, 1-benzyl-3-aminopyrrolidine monohydrobromide (1.68 g) was produced but 48% hydrobromic acid (1.21 g, i.e., an amount of 1.0 molar equivalent of the (R)-1-benzyl-3-aminopyrrolidine) was used instead of concentrated hydrochloric acid. The optical purity was increased to 96.0% e.e. ((R) enantiomeric excess). 1-Benzyl-3-aminopyrrolidine monohydrobromide Melting point: 103° C. to 107° C.

IR (KBr) cm$^{-1}$: 2,149, 1,613, 1,526, 1,467, 1,408, and 1,379

EXAMPLE 3

1-Benzyl-3-aminopyrrolidine (1.51 g) having a chemical purity of 89.9 weight percent and an optical purity of 88.8% e.e. ((R) enantiomeric excess) was dissolved in ethyl acetate (10 g). Acetic acid (0.41 g, i.e., an amount of 0.94 molar equivalents of the (R)-1-benzyl-3-aminopyrrolidine) was added to the mixture. Hexane (30 mL) was added to the solution and the mixture was left for crystallization. The crystals were filtrated and then dried to recover 1-benzyl-3-aminopyrrolidine monoacetate (1.48 g). The optical purity was increased to 93.4% e.e. ((R) enantiomeric excess).

1-Benzyl-3-aminopyrrolidine monoacetate

Melting point: 90° C. to 95° C.

IR (KBr) cm$^{-1}$: 2,224, 1,647, 1,541, 1,474, 1,352, and 1,154

EXAMPLE 4

1-Benzyl-3-aminopyrrolidine (1.42 g) having a chemical purity of 89.9 weight percent and an optical purity of 88.8% e.e. ((R) enantiomeric excess) was dissolved in ethyl acetate (5 g). A solution prepared by dissolving methanesulfonic acid (0.49 g, i.e., an amount of 0.75 molar equivalents of the (R)-1-benzyl-3-aminopyrrolidine) in ethyl acetate (5 g) was added to the mixture. As soon as the solution was added, the crystals precipitated. The crystals were filtrated and then dried to recover 1-benzyl-3-aminopyrrolidine monomethanesulfonate (1.40 g). The optical purity was increased to 95.4% e.e. ((R) enantiomeric excess). 1-Benzyl-3-aminopyrrolidine monomethanesulfonate Melting point: 97° C. to 102° C.

IR (KBr) cm$^{-1}$: 2,149, 1,615, 1,549, 1,453, 1,240, and 1,148

EXAMPLE 5

1-Benzyl-3-aminopyrrolidine (3.38 g) having a chemical purity of 100 weight percent and an optical purity of 90.5% e.e. ((R) enantiomeric excess) was dissolved in isopropyl alcohol (15 g). A 48% solution of hydrobromic acid (3.05 g, i.e., an amount of 0.99 molar equivalents of the (R)-1-benzyl-3-aminopyrrolidine) was added to the solution. The mixture was concentrated by about 5 g under reduced pressure to remove water. The concentrated mixture was stirred at room temperature to allow crystallization. The crystals were filtrated and then dried to recover 1-benzyl-3-aminopyrrolidine monohydrobromide (0.95 g). The optical purity was increased to 99.6% e.e. ((R) enantiomeric excess).

EXAMPLE 6

1-Benzyl-3-aminopyrrolidine (10.17 g) having a chemical purity of 90.3 weight percent and an optical purity of 89.8% e.e. ((R) enantiomeric excess) was dissolved in ethanol (30 g). A 48% of hydrobromic acid (7.84 g, i.e., an amount of 0.94 molar percent solution equivalents of the (R)-1-benzyl-3-aminopyrrolidine) was added to the solution. The mixture was concentrated under reduced pressure to remove water. Ethyl acetate (59 g) was then added to the mixture to allow crystallization. The resultant slurry was heated to about 70°

C. in order to dissolve the crystals entirely. The solution was gradually cooled to allow crystallization. The crystals were filtrated and then dried to recover 1-benzyl-3-aminopyrrolidine monohydrobromide (6.15 g). The optical purity was increased to 100% e.e. ((R) enantiomeric excess).

EXAMPLE 7

1-Benzyl-3-aminopyrrolidine (10.17 g) having a chemical purity of 90.3 weight percent and an optical purity of 89.8% e.e. ((R) enantiomeric excess) was dissolved in ethanol (30 g). Methanesulfonic acid (4.47 g, i.e., an amount of 0.94 molar equivalents of the (R)-1-benzyl-3-aminopyrrolidine) was added to the solution. The ethanol was removed under reduced pressure. Ethyl acetate (54 g) was then added to the mixture to allow crystallization. The resultant slurry was heated to about 79° C. in order to dissolve the crystals entirely. The solution was gradually cooled to allow crystallization. The crystals were filtrated and then dried to recover 1-benzyl-3-aminopyrrolidine monomethanesulfonate (12.12 g). The optical purity was increased to 96.1% e.e. ((R) enantiomeric excess).

The 1-benzyl-3-aminopyrrolidine monomethanesulfonate (2 g) was dissolved in water (5 mL). And then 30% sodium hydroxide was added to the solution to isolate 1-benzyl-3-aminopyrrolidine. The solution was extracted with toluene (20 mL) and then concentrated. Thus, oily 1-benzyl-3-aminopyrrolidine (1.10 g) was recovered.

INDUSTRIAL APPLICABILITY

According to the present invention, as described above, the optical purity of 1-benzyl-3-aminopyrrolidine having a low optical purity can be improved with an inexpensive agent via a simple procedure.

The invention claimed is:

1. A method for improving the optical purity of 1-benzyl-3-aminopyrrolidine, comprising the step of:
converting 1-benzyl-3-aminopyrrolidine into an equimolar salt with an optically inactive acid.

2. The method according to claim 1, wherein the 1-benzyl-3-aminopyrrolidine is an optically active substance.

3. The method according to claim 2, wherein the content of the optically inactive acid is 1 molar equivalent or less of one optical isomer having a higher content of 1-benzyl-3-aminopyrrolidine.

4. The method according to any one of claims 1 to 3, wherein the step of converting comprises:
removing water in a reaction mixture containing an aqueous solution of the optically inactive acid to crystallize the salt by concentration of the mixture.

5. The method according to any one of claims 1 to 3, wherein the step of converting comprises:
mixing 1-benzyl-3-aminopyrrolidine with the optically inactive acid in a solvent to crystallize the salt.

6. The method according to any one of claims 1 to 3, wherein the step of converting comprises:
mixing 1-benzyl-3-aminopyrrolidine with the optically inactive acid in a solvent, or dissolving a salt of 1-benzyl-3-aminopyrrolidine with the optically inactive acid in a solvent; and
cooling the mixture to crystallize the salt.

7. The method according to any one of claims 1 to 3, wherein the step of converting comprises:

mixing 1-benzyl-3-aminopyrrolidine with the optically inactive acid in a solvent, or dissolving a salt of 1-benzyl-3-aminopyrrolidine with the optically inactive acid in a solvent; and
adding a poor solvent to the mixture, or replacing the solvent with a poor solvent to crystallize the salt.

8. The method according to claim 1, wherein the optically inactive acid is at least one acid selected from the group consisting of hydrochloric acid, hydrobromic acid, methanesulfonic acid, and acetic acid.

9. The method according to claim 8, wherein the optically inactive acid is hydrobromic acid or methanesulfonic acid.

10. The method according to claim 8, wherein the step of converting comprises:
removing water in a reaction mixture containing an aqueous solution of the optically inactive acid to crystallize the salt by concentration of the mixture.

11. The method according to claim 8, wherein the step of converting comprises:
mixing 1-benzyl-3-aminopyrrolidine with the optically inactive acid in a solvent to crystallize the salt.

12. The method according to claim 8, wherein the step of converting comprises:
mixing 1-benzyl-3-aminopyrrolidine with the optically inactive acid in a solvent, or dissolving a salt of 1-benzyl-3-aminopyrrolidine with the optically inactive acid in a solvent; and
cooling the mixture to crystallize the salt.

13. The method according to claim 8, wherein the step of converting comprises:
mixing 1-benzyl-3-aminopyrrolidine with the optically inactive acid in a solvent, or dissolving a salt of 1-benzyl-3-aminopyrrolidine with the optically inactive acid in a solvent; and
adding a poor solvent to the mixture, or replacing the solvent with a poor solvent to crystallize the salt.

14. The method according to claim 9, wherein the step of converting comprises:
removing water in a reaction mixture containing an aqueous solution of the optically inactive acid to crystallize the salt by concentration of the mixture.

15. The method according to claim 9, wherein the step of converting comprises:
mixing 1-benzyl-3-aminopyrrolidine with the optically inactive acid in a solvent to crystallize the salt.

16. The method according to claim 9, wherein the step of converting comprises:
mixing 1-benzyl-3-aminopyrrolidine with the optically inactive acid in a solvent, or dissolving a salt of 1-benzyl-3-aminopyrrolidine with the optically inactive acid in a solvent; and
cooling the mixture to crystallize the salt.

17. The method according to claim 9, wherein the step of converting comprises:
mixing 1-benzyl-3-aminopyrrolidine with the optically inactive acid in a solvent, or dissolving a salt of 1-benzyl-3-aminopyrrolidine with the optically inactive acid in a solvent; and
adding a poor solvent to the mixture, or replacing the solvent with a poor solvent to crystallize the salt.

* * * * *